United States Patent
Diaz et al.

(10) Patent No.: US 6,932,987 B1
(45) Date of Patent: Aug. 23, 2005

(54) CHEMICAL COMPOSITION AND METHOD FOR ENHANCING METABOLISM

(76) Inventors: Jose A. Diaz, 3326 Mary St., Suite 603, Coconut Grove, FL (US) 33133;
Eduardo M. Naranjo, 3326 Mary St., Suite 603, Coconut Grove, FL (US) 33133

( * ) Notice: Subject to any disclaimer, the term of this patent is extended or adjusted under 35 U.S.C. 154(b) by 0 days.

(21) Appl. No.: 10/446,619

(22) Filed: May 28, 2003

Related U.S. Application Data

(60) Provisional application No. 60/383,885, filed on May 29, 2002.

(51) Int. Cl.$^7$ ...................... A01N 65/00; A61K 35/78; A61K 39/385
(52) U.S. Cl. .................. 424/725; 424/195.1; 424/729; 424/736; 424/756
(58) Field of Search .................. 424/195.1, 725, 424/756, 729, 736

(56) References Cited

U.S. PATENT DOCUMENTS

| | | | |
|---|---|---|---|
| 6,426,077 B1 * | 7/2002 | Grace et al. | 424/400 |
| 6,565,847 B1 * | 5/2003 | Gorsek | 424/93.45 |
| 6,733,793 B2 * | 5/2004 | Pacioretty et al. | 424/646 |
| 2003/0082168 A1 * | 5/2003 | Yegorova | 424/94.61 |

FOREIGN PATENT DOCUMENTS

JP    10218765 A   *   9/1998

OTHER PUBLICATIONS

Ohr, L. No Claims are allowed. Shedding Light on Weight Issues; Food Technology, 2002 (Aug.), 56 (8), 125-128, Abstract from Frosti Database only provided.*

* cited by examiner

*Primary Examiner*—Christopher R. Tate
*Assistant Examiner*—Jennifer Ione Harle
(74) *Attorney, Agent, or Firm*—Malloy & Malloy, P.A.

(57) ABSTRACT

An innovative and synergistic chemical composition is developed for enhancing a person's metabolism. Specifically, the chemical composition aids in increasing the thermogenic activity of the body, which encourages the metabolic conversion of the foods consumed by the person. This results in a loss of body fat and weight, without adversely affecting the person's nervous or circulatory systems. In addition, a method is presented wherein the person ingests a recommended dosage of the chemical composition prior to engaging in physical exercise, thereby allowing the chemical composition to be readily utilized by many of the people who may benefit from its effects.

22 Claims, No Drawings

CHEMICAL COMPOSITION AND METHOD FOR ENHANCING METABOLISM

CLAIM OF PRIORITY

The present application is based on and a claim to priority is made under 35 U.S.C. Section 119(e) to provisional patent application currently pending in the U.S. Patent and Trademark Office having Ser. No. 60/383,885 and a filing date of May 29, 2002.

BACKGROUND OF THE INVENTION

1. Field of the Invention

The present invention relates to a chemical composition and a method for enhancing metabolism. Specifically, the present invention provides an innovative, synergistic chemical composition which aids in increasing thermogenic activity, thereby encouraging metabolic conversion of the foods consumed by a person, resulting in a loss of body fat and weight, without adversely affecting the nervous or circulatory systems. The present invention also comprises a method wherein the person ingests a recommended dosage of the chemical composition prior to exercising, thereby allowing the invention to be readily used by many of the people who may benefit from the effects of the composition.

2. Description of the Related Art

It is well known that in today's fast paced society many, if not a majority of people do not maintain a proper balance of diet and physical activity as required to sustain a human body in optimum condition. A result of the failure to maintain this proper balance is, at a minimum, a reduction in a person's ability to perform, both mentally and physically. This subsequent reduction in performance translates into a reduction in productivity which, when compounded by the number of people exhibiting this condition, can result in an overall decrease in productivity, creativity, and/or innovation in society as a whole. In addition, a decrease in the person's ability to perform, either physically or mentally, may also have negative impacts upon their outlook and well-being with respect to other personal aspects of their lives.

It is also well understood that the reason that many people fail to maintain the proper balance between diet, exercise, and rest is the increasingly active lifestyles which today's society dictates. One direct result of this active lifestyle is an increased reliance on pre-packaged, processed, or other types of "fast food" dining solutions, purely in the interest of convenience (i.e. a reduction in the time associated with preparation and/or consumption), rather than the nutritional value of a meal. Often times these types of pre-packaged, processed, or other types of "fast foods" do not contain the proper balance of carbohydrates, proteins, and fats which the body can metabolize in an efficient manner. In addition, many of these pre-packaged, processed, or other types of "fast foods" do not contain sufficient quantities of the vitamins which the body requires to properly metabolize the foods consumed, if in fact, many contain any vitamins at all.

Similarly, many people fail to maintain any regular program of regular physical exercise, whether due to time constraints or other reasons, even though it is well known that exercise is also required to assure proper metabolization of the foods the person consumes. Specifically, the body may metabolize food into simple sugars, which are maintained in the bloodstream, such that they may be readily converted to energy in the cells of the body as required due to physical exercise or other expenditures of energy. Alternatively, the body may metabolize food into more complex molecules, such as glycogens, which the body then stores for later conversion into simple sugars and subsequent conversion into energy by the body. Thus, as the person exercises, the simple sugars in the bloodstream are converted to energy in the cells of the body and the glycogens are converted into simple sugars to assure that an adequate supply of energy is available.

However, when the person does not maintain a proper balance between the types or amounts of food consumed, the vitamins required for proper metabolization, and/or the energy physically expended by the body through, for example, a regular program of physical exercise, the foods consumed by the person may not be completely metabolized, in which case by-products may be stored in the body as fat, which is not efficiently recoverable for subsequent conversion into energy. Thus, the incomplete metabolization of the food consumed by the person may have a direct impact on their weight, and it is well known that an overweight person is more susceptible to a variety of conditions which are detrimental to the person's health, including an increased risk of heart disease, stroke, or diabetic conditions, to name just a few. In addition, given the focus in today's society on physical appearances, an overweight person may also be subject to negative social consequences as well.

Given the fact that in today's society a majority of people do not maintain a proper balance of diet and physical activity, there is a need for an aid, such as a chemical composition, which enhances the body's metabolic functions to assist in maintaining a person's health and well-being. Furthermore, such a chemical composition should ideally increase thermogenic activity and metabolism, thereby encouraging metabolic conversion of the foods the person consumes, resulting in a loss of body fat and weight, without adversely affecting the nervous or circulatory systems. In addition, a method is required which may be readily practiced by persons who may benefit from the effects of such a chemical composition, and which is easily incorporated into their active lifestyles, thereby assuring the benefits of the chemical composition to a wide segment of society.

SUMMARY OF THE INVENTION

The present invention is designed to satisfy the aforementioned needs in the art and is believed to represent a significant advance in improving a person's health and well-being by providing an innovative, synergistic chemical composition which increases thermogenic activity and metabolism, thereby encouraging caloric conversion of the food the person consumes and a resultant loss in body fat and weight without affecting the nervous system. In addition, the present invention encompasses a method which may be readily practiced by one or more persons who will benefit from the effects of this innovative chemical composition.

The chemical composition of the present invention comprises a mixture of conjugated linoleic acid, green tea extract, and L-carnitine, along with, in a preferred embodiment, other components. Conjugated linoleic acid or "CLA" is a fatty acid reported to aid in the reduction of body fat, while green tea extract is believed to augment thermogenesis, the conversion of body fat to energy, or both. In addition, L-carnitine, a nutrient, is provided to increase the utilization of fat, in the muscles, as an energy source. The chemical composition of the present invention preferably also includes capsaicin, which has been shown to activate heat loss and heat production, and *Citrus aurantium*, also known as orange bitters, thought to soothe stomach disturbances and enhance heat production.

In a preferred embodiment of the invention, the innovative chemical composition comprises predetermined amounts of the aforementioned components. More particularly, each component is present in an amount corresponding to an approximate weight ratio relative to the other components. For example, in one embodiment of the present invention, CLA, green tea extract, and *Citrus aurantium* are each present in approximately equal amounts by weight, while L-carnitine is present in an amount of approximately two (2) parts by weight per one (1) part by weight of CLA. In addition, capsaicin is present in an amount of approximately one-half (½) part by weight per one (1) part by weight of CLA.

As another example, in one embodiment of the present invention, capsules or tablets are prepared containing approximately 50 milligrams (mg) each of CLA, green tea extract, and *Citrus aurantium*; approximately 100 mg of L-carnitine; and approximately 25 mg of capsaicin. The daily dosage of the innovative, synergistic chemical composition of the present invention may comprise one or, preferably, two capsules or tablets, each containing the above amounts of the these active components. In addition to the above mentioned active components, each capsule or tablet may contain one or more inert ingredients such as binders, fillers and/or coatings to facilitate ingestion.

The innovative chemical composition of the present invention may also be expressed in terms of weight percentages of the active components, wherein CLA, green tea extract, and *Citrus aurantium* preferably each comprise approximately 15% to 20% by weight; L-carnitine preferably comprises approximately 30% to 40% by weight; and capsaicin comprises approximately 7.5% to 10% by weight.

Additionally, a method for utilizing the innovative chemical composition of the present invention is disclosed, wherein the method comprises making the chemical composition containing the aforementioned active components, forming a capsule or tablet of generally about 500 mg to 600 mg total weight, although a smaller capsule of about 425 mg may be used instead, and having a person ingest at least one but preferably two of these capsules or tablets with generally about eight ounces of water approximately one hour prior to engaging in physical exercise. As an alternative, however, the capsules or tablets may be taken by the person first thing in the morning.

A primary object of the present invention is to provide an innovative, synergistic chemical composition and method for enhancing metabolism, which aids in increasing thermogenic activity, thereby encouraging metabolic conversion of the food the person consumes, resulting in a loss of body fat and weight.

One advantage of the chemical composition and method according to the present invention is that the increase in metabolism or thermogenic activity is believed to occur without adversely affecting the person's nervous or circulatory systems.

Another advantage of the chemical composition and method according to the present invention is that the production of homocysteine, an irritant of the endothelial cells in the wall of blood vessels which is associated with a risk of heart disease, may also be reduced.

A further feature of the chemical composition according to the present invention is that it is moisture activated and, therefore, may be formed into and stored as conveniently sized capsules, tablets, or other suitable delivery mechanism, until being ingested by the person, and activated by coming into contact with bodily secretions, water, or other liquid.

These and other objects, features and advantages of the present invention will become readily apparent from the detailed description, which follows.

DETAILED DESCRIPTION OF THE PREFERRED EMBODIMENT

The present invention is directed towards an innovative, synergistic chemical composition which enhances metabolism in the human body. The present invention is also directed to a method for a person to obtain the benefits of the innovative chemical composition, by ingesting a recommended dosage of the composition.

In particular, the present invention provides an innovative, synergistic chemical composition which, when ingested, increases a person's metabolism, thereby increasing the reduction of the foods the person consumes into simple sugars, such as glucose, so that they may be readily absorbed by the cells of the body and converted to energy therein. As a result, the amount of by-products generated from the metabolism of the food the person consumes and which may otherwise be stored in the body as glycogens or, more detrimentally, stored as fats, are reduced. In particular, when the chemical composition of the present invention is ingested by the person prior to physical exercise, the components synergistically act to increase the absorption of glucose by the cells of the body and the subsequent conversion of the glucose into energy. As such, the body will proceed to further reduce the other by-products of metabolism into glucose to replace the sugar absorbed and converted into energy, thereby preventing the storage of these by-products in the body in the form of glycogens or fats. Furthermore, the innovative chemical composition of the present invention promotes the conversion of the fats previously stored in the body into simpler compounds which may then be utilized to provide the body with energy.

In accordance with the present invention, the chemical composition is moisture activated such that the active components remain inert until they come into contact with water, bodily fluids or other liquids. Thus, the chemical composition can be formed into capsules, tablets, or any other suitable delivery mechanisms, preferably conveniently sized for ingestion by the person, and stored in a dry place until they are needed.

The innovative chemical composition of the present invention primarily comprises a mixture of L-carnitine (3-hypodroxy-4-N-trimethylaminobutyric acid), a nutrient which is provided to aid in the utilization of the fats stored in the muscles of the body, as a source of usable energy (i.e. by reduction of fats into simpler compounds), conjugated linoleic acid or "CLA", and green tea extract, although in more preferred embodiments the inventive composition includes other components. Specifically, one preferred embodiment of the chemical composition comprises L-carnitine, conjugated linoleic acid, green tea extract, *Citrus aurantium*, and capsaicin, each of which is discussed more fully hereinafter. Conjugated linoleic acid, also known as CLA, is a fatty acid reported to aid in the reduction of body fat, and as such, is similar to green tea extract, which is an active component that has been shown to increase thermogenesis and reduce fat. The *Citrus aurantium*, also known as orange bitters, is provided in the innovative chemical composition and is thought to be a digestive tonic helpful in soothing stomach disturbances and increase heat production.

Finally, capsaicin, a chemical derived from a hot pepper, and which is known to activate heat production that contributes to weight loss, is included in the preferred embodiment of the innovative, synergistic chemical composition of the present invention.

The chemical composition of the present invention preferably comprises predetermined amounts of the aforesaid active components. Specifically, in at least one embodiment, the CLA, green tea extract, and *Citrus aurantium* are each preferably present in approximately equal amounts, by weight, while the L-carnitine is present in an amount of approximately two (2) parts by weight per one (1) part by weight of CLA. In addition, in this embodiment, capsaicin is present in an amount of approximately one-half (½) part by weight per one (1) part by weight of CLA.

By way of example, in at least one embodiment of the present invention, capsules or tablets are prepared for ingestion by the person each containing approximately 50 milligrams (mg) each of CLA, green tea extract, and *Citrus aurantium*; approximately 100 mg of L-carnitine; and approximately 25 mg of capsaicin. The daily dosage of the innovative, synergistic chemical composition of the present invention may comprise one or more of these capsules or tablets, each containing the aforementioned amount of each of these active components. In addition to the aforementioned active components, each capsule or tablet may contain one or more inert ingredients, such as binders, fillers and/or coatings, to facilitate their ingestion by the person.

The innovative, synergistic chemical composition of the present invention may also be expressed in terms of each components percentage of the total weight of the composition, wherein L-carnitine preferably comprises approximately 30% to 40% by weight; CLA, green tea extract, and *Citrus aurantium* each comprise approximately 15% to 20% by weight; and capsaicin comprises approximately 7.5% to 10% by weight.

In addition to the aforementioned embodiment, at least one alternate embodiment of the innovative, synergistic chemical composition of the present invention includes additional active components. In this alternate embodiment, ascorbic acid, or Vitamin C, which reportedly may aid in faster weight reduction, is preferably present in an amount approximately equal to the amount of L-carnitine, by weight. Also, Vitamin B-Complex (which may include, for example, Vitamins B-1, B-2, B-6, B-12, niacin, folate and pantothenic acid) and ginger extract are each preferably present in amounts equal to the weight of capsaicin present. Vitamin B-Complex has been reported to protect against an increase in homocysteine production in the body during weight loss, while the ginger extract, which is derived from the root of the plant, *Zenziber officinale*, exhibits anti-cholesterol and anti-atherogenic effects.

Furthermore, this alternate embodiment and/or others may also comprise taurine, an amino acid which helps reduce cholesterol; lecithin, a phospholipid which exhibits hypocholesterolemic and anti-atherogenic properties; and inositol phosphate, a nutrient associated with the metabolism of fatty acids. Each of these components are preferably present in an amount approximately equal to that of CLA, by weight.

As previously indicated, the innovative chemical composition of the present invention is preferably formed into either capsules or tablets. In the alternate embodiment described above, each capsule or tablet may comprise 425 mg that includes at least the following: 100 mg each of L-carnitine and ascorbic acid; 50 mg each of CLA, green tea extract, taurine, lecithin, and inositol phosphate; and 25 mg each of capsaicin, Vitamin B-Complex, and ginger extract. This embodiment may additionally include, but does not have to include, 50 mg of Citrus aurantium (orange bitters) as well. Upon contact with moisture, such as by being ingested with a glass of water, the composition, whether in tablet or capsule form, begins to break down and the components become synergistically active.

Similar to the previously disclosed embodiment of the chemical composition, this alternate embodiment may also be expressed in terms of each component's percentage of the total weight of the composition. Thus, in this alternate embodiment, L-carnitine and Vitamin C each preferably comprise approximately 15% to 20% by weight of the composition; CLA, green tea extract, *Citrus aurantium*, taurine, lecithin, and inositol phosphate each comprise approximately 7.5% to 10% by weight of the composition; and capsaicin, Vitamin B-complex, and ginger extract each comprise approximately 3% to 5% by weight of the composition.

The present invention further contemplates a method for utilization of the innovative chemical composition which comprises making the composition by adding together at least some of the aforementioned active components, forming a tablet or capsule of generally about 500 to 600 mg, and having the person ingest at least one of the capsules with generally about eight ounces of water approximately between one-half hour and one hour prior to engaging in physical exercise. Ideally, the person will ingest one or two of the capsules prior to exercising, but may ingest three or more capsules if the person has consumed an especially large meal and/or a meal that has a particularly high sugar content. Upon ingestion by the person, each capsule begins to disintegrate and releases or otherwise facilitates activation of the chemical composition contained therein, typically in about thirty (30) minutes, and often in less time. As an alternative, the person may ingest the one or more capsules or tablets first thing upon waking up in the morning. In addition, the person may be directed to ingest generally about eight ounces of water upon waking, and ideally, an additional step of having the person ingest generally about eight ounces of distilled water between meals.

Since many modifications, variations and changes in detail can be made to the described preferred embodiment of the invention, it is intended that all matters in the foregoing description be interpreted as illustrative and not in a limiting sense. As one example, while the innovative chemical composition disclosed herein has been referred to as useful if consumed by and implemented with humans, it is contemplated that other animals may treated and derive benefits from the composition, and their treatment should also be considered within the scope and spirit of the present invention. Similarly, pharmacologically acceptable substitutes of components described in the inventive composition may be used, such as but not limited to, pharmacologically acceptable salts of L-carnitine. Thus, the scope of the invention should be determined by the appended claims and their legal equivalents.

What is claimed is:

1. A chemical composition which enhances metabolism, wherein said composition is formed into tablets, each of said tablets comprising:
   a) approximately 100 mg of L-carnitine;
   b) approximately 50 mg of conjugated linoleic acid;
   c) a predetermined amount of ginger extract;
   d) approximately 50 mg of green tea extract;
   e) approximately 50 mg of *Citrus aurantium*; and
   f) approximately 25 mg of capsaicin.

2. The chemical composition as recited in claim 1 wherein said amount of said L-carnitine is approximately 30% to 40% by weight of said composition; said amounts of said conjugated linoleic acid, said green tea extract, and said *Citrus aurantium* are each approximately 15% to 20% by weight of said composition; and said amount of said capsaicin is approximately 7.5% and 10% by weight of said composition.

3. A chemical composition as recited in claim 1 wherein each of said tablets further comprises approximately 100 mg of ascorbic acid.

4. A chemical composition as recited in claim 1 wherein each of said tablets further comprises approximately 50 mg of taurine.

5. A chemical composition as recited in claim 1 wherein each of said tablets further comprises approximately 50 mg of lecithin.

6. A chemical composition as recited in claim 1 wherein each of said tablets further comprises approximately 50 mg of inositol phosphate.

7. A chemical composition as recited in claim 1 wherein each of said tablets further comprises approximately 25 mg of Vitamin B-Complex.

8. A chemical composition as recited in claim 1 wherein each of said tablets further comprises approximately 25 mg of said ginger extract.

9. The chemical composition as recited in claim 1 wherein said amount of said L-carnitine is approximately 15% to 20% by weight of said composition; said amounts of said conjugated linoleic acid, said green tea extract, and said *Citrus aurantium* are each approximately 7.5% to 10% by weight of said composition; and said amount of said capsaicin is approximately 3% to 5% by weight of said composition.

10. A chemical composition as recited in claim 9 further comprising ascorbic acid at approximately 15% to 20% by weight of said composition.

11. A chemical composition as recited in claim 9 further comprising taurine at approximately 7.5% to 10% by weight of said composition.

12. A chemical composition as recited in claim 9 further comprising lecithin at approximately 7.5% to 10% by weight of said composition.

13. A chemical composition as recited in claim 9 further comprising inositol phosphate at approximately 7.5% to 10% by weight of said composition.

14. A chemical composition as recited in claim 9 further comprising Vitamin B-Complex at approximately 3% to 5% by weight of said composition.

15. A chemical composition as recited in claim 9 further comprising said ginger extract at approximately 3% to 5% by weight of said composition.

16. A method of enhancing metabolism in a person, said method comprising:
  making a chemical composition by adding together approximately 100 mg of L-carnitine; 50 mg each of conjugated linoleic acid, green tea extract, and *Citrus aurantium*; and 25 mg of capsaicin; and a predetermined amount of ginger extract forming the chemical composition into a tablet; and
  having the person ingest at least one tablet with approximately eight ounces of water approximately one hour prior to engaging in physical exercise.

17. A method as recited in claim 16 wherein making the chemical composition further includes adding approximately 100 mg of ascorbic acid.

18. A method as recited in claim 16 wherein making the chemical composition further includes adding approximately 50 mg of taurine.

19. A method as recited in claim 16 wherein making the chemical composition further includes adding approximately 50 mg of lecithin.

20. A method as recited in claim 16 wherein making the chemical composition further includes adding approximately 50 mg of inositol phosphate.

21. A method as recited in claim 16 wherein making the chemical composition further includes adding approximately 25 mg of Vitamin B-Complex.

22. A method as recited in claim 16 wherein making the chemical composition further includes adding approximately 25 mg of said ginger extract.

* * * * *